United States Patent [19]

Hagemeyer, Jr. et al.

[11] 3,979,432

[45] Sept. 7, 1976

[54] PREPARATION OF NITRILES

[75] Inventors: Hugh J. Hagemeyer, Jr.; Jerry D. Holmes, both of Longview, Tex.

[73] Assignee: Eastman Kodak Company, Rochester, N.Y.

[22] Filed: Oct. 6, 1975

[21] Appl. No.: 620,099

Related U.S. Application Data

[63] Continuation-in-part of Ser. No. 481,711, June 21, 1974, abandoned.

[52] U.S. Cl. .............................. 260/465.2; 203/14; 203/61; 203/69
[51] Int. Cl.² ...................................... C07C 120/08
[58] Field of Search ........................ 203/24, 38, 61; 260/465.2

[56] References Cited
UNITED STATES PATENTS

| | | | |
|---|---|---|---|
| 2,177,619 | 10/1939 | Nicodemus et al. | 260/465.2 |
| 2,229,219 | 1/1941 | Oxley et al. | 260/465.2 |
| 2,732,397 | 1/1956 | Hull | 260/465.2 |

*Primary Examiner*—Joseph Paul Brust
*Attorney, Agent, or Firm*—George P. Chandler; Daniel B. Reece, III

[57] ABSTRACT

An improved process for the production of aliphatic nitriles having two to six carbon atoms by the reaction of an aliphatic carboxylic acid with ammonia in the presence of a catalyst followed by effluent distillation. The improvement lies in the addition of a portion of the aliphatic carboxylic acid after the reactor but before distillation whereby ammonium carboxylate formed in the reaction and dissociated by distillation is reformed to the carboxylate thus preventing the escape of dissociated ammonia and whereby the aliphatic carboxylic acid portion is recycled to the reaction.

5 Claims, 1 Drawing Figure

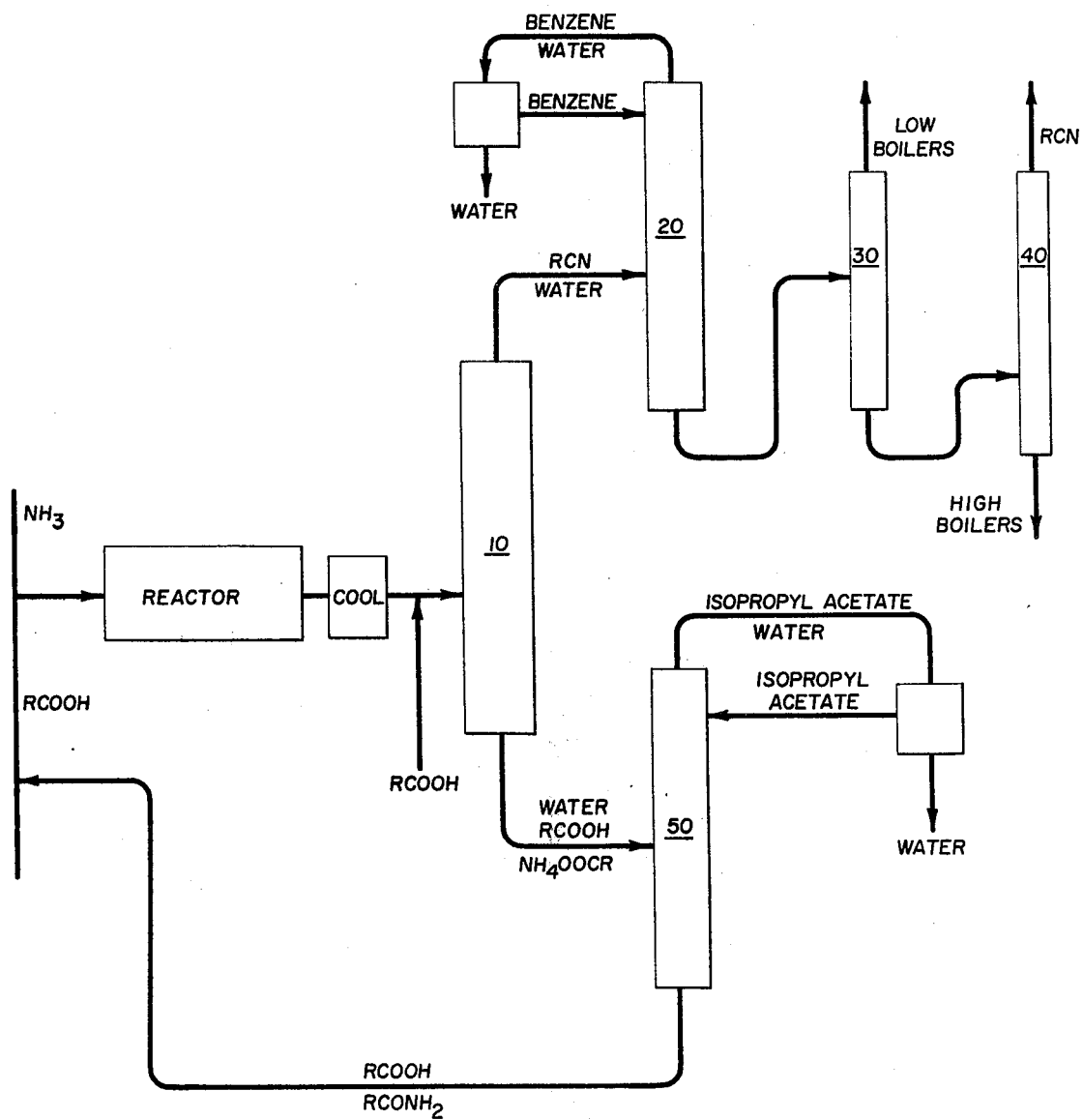

PREPARATION OF NITRILES

This is a continuation-in-part application of Serial No. 481,711, filed June 21, 1974, now abandoned.

This invention relates to an improved process for the preparation of nitriles. More particularly, this invention relates to the following improvements for producing nitriles by the vapor phase acid catalyzed process of reacting a carboxylic acid with ammonia. These improvements include:

1. Increased yield to nitrile from ammonia by converting the unreacted ammonia to ammonium carboxylate then dehydrating to amide and recycling the amide.
2. Prevention of ammonium carbonate formation in the vent lines in the distillation system.
3. Prevention of nitrile contamination by unreacted ammonia.
4. Prevention of organic contamination of the effluent water to avoid water pollution.

The formation of nitriles by the reaction of an aliphatic carboxylic acid with ammonia in the presence of a suitable catalyst is known. See, for example, U.S. Pat. Nos. 2,732,397 and 2,808,426. This reaction occurs in three steps as shown in Equations 1, 2, and 3.

1. $RCOOH + NH_3 \rightleftarrows RCO\bar{O}NH_4+$

2. $RCO\bar{O}NH_4 + \rightleftarrows RCONH_2 + H_2O$

3. $RCONH_2 \rightleftarrows RC \equiv N + H_2O$

The corresponding ammonium carboxylate is first formed (Equation 1) from the acid and ammonia and is then dehydrated to amide which is readily dehydrated to give the nitrile (Equation 3). Thus if amide is added to the acid and ammonia feed going to the reactor, it is readily converted into the corresponding nitrile. This in effect substantially increases the capacity of a given reactor for nitrile production (U.S. Pat. No. 2,732,397).

In our process the aliphatic acid and ammonia are reacted together at 350° to 500°C. and atmospheric pressure to produce the corresponding nitrile in 70 to 80 percent conversion. We have found that 400° to 450°C. is an effective temperature range for this reaction. A suitable catalyst for this process is phosphoric acid on alumina or suitable metal oxides as referred to in U.S. Pat. No. 2,732,397.

As shown in U.S. Pat. No. 2,732,397, an undesirable side reaction the acid can undergo is its conversion into a ketone and carbon dioxide.

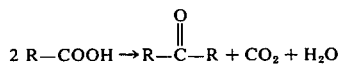

Thus if excess acid is fed to the reactor, excessive amounts of by-product ketone are formed from the acid. Formation of the ketone represents a direct yield loss from the acid and also, very significantly, the ketone interfers with the azeotropic drying of the nitrile. Excessive ketone can cause the azeotropic agent such as benzene to solubilize in the water and prevent adequate separation by decantation. Also the ketones can form azeotropes with nitrile and water which interfer with product purification.

The degree of ketone formation from feeding excess acid to the reactor has been determined for the production of acetonitrile and should be representative for other aliphatic nitriles. We found that feeding a 10 percent excess of acetic acid over ammonia as compared to feeding 10 percent excess ammonia gave a 3.6 fold increase in the amount of acetone formed. Based on prior art and our studies it is very clear that in a practical commercial process for the production of nitriles from ammonia and an aliphatic carboxylic acid excess acid in the reactor feed should be avoided if at all possible.

Processes normally operated with a slight excess of ammonia in the reactor minimize ketone formation. However, this results in free ammonia in the purification system. In these processes acid conversion reaches a maximum of about 70 to 80 percent. The unreacted acid and ammonia combine in the cooled aqueous layer to form ammonium carboxylate in the reactor effluent. These ammonium salts are weakly associated and when heated rapidly, lose ammonia as a gas unless it is trapped. Dissociation of the ammonium carboxylate occurs during distillation with substantial loss of ammonia. Thus, excess ammonia from the reactor and ammonia from dissociation of the ammonium salts is lost out the vent system during product purification. The lost ammonia represents a direct yield loss to nitrile.

In addition to the yield loss, ammmonia contamination of nitrile product and also effluent water from the process normally occurs. These then have to be treated by additional processing to remove alkalinity. A portion of the ammonia also reacts with carbon dioxide in the off gas from the process to form ammonium carbonate which plugs the vent lines and vent condensers.

From the above it is seen that nitrile reactions with excess acid result in undesirable ketone formation. Reactions with excess ammonia result in ammonia loss.

In accordance with this invention these undesirable effects are minimized by feeding to the reactor effluent prior to distillation a portion of the acid fed to the reactor in conventional processes. This acid is then recycled from the purification system to the reactor.

It is thus an object of the process according to this invention to both minimize ketone formation and ammonia loss in a nitrile reaction.

It is another object of the process according to one aspect of this invention to minimize the loss of excess ammonia from the reactor and the production of ammonium carbonate in the above described nitrile process. Another object according to this invention is to minimize the loss of ammonia which occurs from the dissociation of ammonium carboxylates during distillation. A still further object of this invention is to minimize the loss of ammonia from the ammonium carboxylate and to convert the ammonium carboxylate into an aliphatic amide. Yet another object of this invention is to utilize the aliphatic amide produced in the aforedescribed conversion to recycle to the nitrile reactor without ammonia loss resulting in an aliphatic nitrile and effluent water free of ammonia. Another objective of this invention is to provide a process by which the effluent water is free of organic contamination. Removal of dissolved ammonium carboxylate and excess acid from the water provides a pollution free process.

These objects are accomplished in accordance with this invention which in its broader aspects comprises separating a calculated part of the acid normally fed to the reactor and feeding it into the reactor effluent. This in effect provides two feed points for the acid used in the reaction but as will be illustrated provides a method for operating the nitrile reactor with a slight excess of ammonia without ammonia loss in the purification system. By addition of a portion of the acid feed into the cooled reactor effluent (approximately 50°C.) free ammonia from the reactor is converted to ammonium carboxylate. This is particularly beneficial since in our invention as we have found that by adding a sufficient excess of acid over ammonium carboxylate prior to distillation, ammonia loss is avoided during distillation and by-product ketone formation is avoided. Even though the ammonium carboxylate dissociates during distillation, the released ammonia reacts with the excess acid so fast the ammonium carboxylate is re-formed before ammonia can escape. The amount of excess acid over ammonium carboxylate salt is important to provide essentially complete ammonia recovery.

According to one aspect of the invention an aliphatic nitrile is produced by reacting gaseous ammonia with an aliphatic carboxylic acid to form a product including unreacted ammonia, an aliphatic nitrile, and water containing an ammonium carboxylate salt. This product is distilled to separate the aliphatic nitrile from the ammonium carboxylate salt, but before distillation an aliphatic carboxylic acid is added to the reactor effluent at a ratio in the range of from about one mole carboxylic acid to one mole ammonium carboxylate to about 4 moles carboxylic acid to one mole ammonium carboxylate whereby less than one percent of the ammonia escapes from the distillation column and undesirable ketone formation does not occur.

According to a still further aspect of the invention a base stream comprising water, carboxylic acid, and ammonium carboxylate is taken from the distillation column and dehydrated to yield a stream comprising carboxylic acid and an aliphatic amide which is recycled to the nitrile reactor.

According to yet another aspect of the invention the molar ratio of carboxylic acid to ammonium carboxylate is about 2/1.

According to yet a still further aspect of the invention the aliphatic carboxylic acid contains from 2 to 6 carbon atoms.

The invention will be more fully understood by reference to the following description and attached drawing in which the single figure is a schematic representation in the nature of a flow sheet illustrating the various steps involved in a typical process carried out in accordance with our invention.

Ammonia and an aliphatic acid are fed to the reactor at relative rates in the range of 1/1 to 1.15/1 moles ammonia per mole of aliphatic acid. Catalyst and reaction conditions for preparation of nitrile are described above. A description for producing acetonitrile is given and is representative of the aliphatic nitriles.

The effluent stream from the reactor producing acetonitrile contains about 40 to 50 percent acetonitrile, 6 to 10 percent ammonium acetate and 1 to 3 percent ammonia, acetone, and acetamide. The remainder of the effluent is made up of water. The effluent stream from the reactor is cooled to about 50°C. and then fed to Distillation Column 10 but prior to entering such column acetic acid is added to the effluent stream. The acetic acid added here is a portion of the total amount used to react with the ammonia in the reactor to give acetonitrile in conventional processes.

Acetic acid is added to the effluent stream at a molar ratio of from about 1/1 to 4/1 moles of acid to moles of ammonium acetate. Preferred is a 2/1 ratio of acid to ammonium carboxylate.

In the Distillation Column 10 the acetonitrile water azeotrope is taken overhead and fed to Distillation Column 20 where the water is removed by azeotropic distillation utilizing benzene. Pure acetonitrile is taken overhead after removal of high boilers in Distillation Column 40 and low boiler removal in Distillation Column 30. This purification process is conventional and forms no part of the invention.

The base product from Distillation Column 10 containing 41 to 62 percent water, 16 to 45 percent acetic acid, and 14 to 22 percent ammonium acetate is fed to Distillation Column 50. In Distillation Column 50 a suitable azeotroping agent such as isopropyl acetate is used to remove the water. The head temperature of Column 50 is held below about 80°C. which is slightly above the azeotropic boiling point of 76.6°C. for water and isopropyl acetate with the base temperature greater than 150°C. The base stream from Column 50 contains acetic acid and acetamide which are recycled to the nitrile reactor. In the reactor the acetic acid reacts with the ammonia to form the previously described products including acetonitrile while the acetamide is dehydrated to the acetonitrile.

In the process it has been found that the addition of a sufficient portion of the carboxylic acid usually fed to the nitrile reactor into the distillation system prior to distillation results in an ammonia loss of less than one percent of ammonium carboxylate feed as compared to an 18 to 20 percent loss when no excess acid is added. Further, the aliphatic nitrile distilled from Column 40 passes usual alkalinity specifications (less than 0.45 ml 0.1N HCl per 100 ml sample for neutralization) without additional treatment.

Furthermore the water taken overhead in Column 50 is separated from the azeotroping agent by simple decantation. This water contains minimal organic contamination and can be discharged without polluting the environment.

The following examples are presented as illustrative of this invention:

EXAMPLE 1

Ammonia and acetic acid are reacted together resulting in an effluent stream fed to Distillation Column 10 consisting of acetonitrile, ammonium acetate, acetone by-product, and water. To this reactor effluent of 560 grams is added 125 grams acetic acid to give a mixture containing 1.78 moles of acetic acid, 0.86 mole ammonium acetate, and 5.9 moles acetonitrile. The Distillation Column 10 is made up of a 10 plate section, a feed plate, and a top part of 15 plates. The column is operated at a 25 percent takeoff and the distillation is stopped when the head temperature reaches 87°C. which is sufficiently above the boiling point of the acetonitrile-water azeotrope of 76.5°C. to give complete removal of acetonitrile from the base. An overhead fraction of 286 grams is collected which contains 0.0035 mole ammonia and an off-gas line scrubber collected 0.004 mole ammonia. This gives a total ammonia loss of 0.0075 mole corresponding to 0.9 percent of ammonium acetate charged to the distillation step.

Distillation Column 20 which is similar to Column 10 is charged with 260 grams of the overhead product containing 218 grams acetonitrile, 37 grams water, and 5 grams of acetone. The top temperature is held to a maximum 70°C. with a 25 percent takeoff. Benzene is fed to the feed plate at 150 ml per hour and is collected with water overhead. After separation of the water and benzene, the benzene is recycled to the column until water removal is completed. The dried acetonitrile, after low boiler removal, is taken overhead as a pure product. This final product requires less than 0.35 ml 0.1N HCl per 100 ml of sample for neutralization. Specifications are 0.45 ml 0.1N HCl per 100 ml sample. Total acetonitrile accountability is 99 percent.

To a 20 plate Column 50 is charged 345 grams of base product from Distillation Column 10. This product contains 1.7 moles acetic acid and 0.82 mole ammonium acetate with the remainder being mostly water. The percent takeoff is set at 25 and the overhead temperature is held below 80°C. The base temperature is maintained at about 180°C. Isopropyl acetate is pumped into the feed plate at 250 ml per hour and collected overhead with water. After separating the water, the isopropyl acetate is recycled to the column until no more water comes overhead. After water removal is complete, the base product contains 1.6 moles acetic acid and 0.82 mole acetamide. This is a 97 percent conversion and yield of ammonium acetate to acetamide starting with the feed to Distillation Column 10. The acetic acid and acetamide can be then recycled to the reactor for conversion into acetonitrile.

EXAMPLE 2

This example illustrates the loss of ammonia by dissociation of ammonium acetate during distillation which occurs when only a small amount of free acetic acid is added to the product prior to distillation. To the effluent from the nitrile reactor is added only a small amount of acetic acid to obtain an essentially typical stream containing 0.1 mole acetic acid and 0.83 mole ammonium acetate in addition to acetonitrile. This stream is charged to a 20 plate distillation column where distillation is carried out at a 25 percent top takeoff up to a maximum temperature of 80°C. Analysis of the overhead product and gas line scrubbers gives a total of 0.15 mole ammonia. The base product contains 0.27 mole acetic acid and 0.67 mole ammonium acetate corresponding to a net increase of acetic acid of 0.17 mole and a decrease of 0.16 mole ammonium acetate. These results show a decomposition of the ammonium acetate during distillation without reformation and a loss of ammonia of 18 to 20 percent based on the ammonium acetate.

Further loss of ammonia may occur when ammonium acetate is dehydrated to acetamide with only a small excess of acetic acid present as follows. To a packed column is charged a mixture of 1.36 moles ammonium acetate and 0.35 mole acetic acid in an aqueous solution. Distillation of this mixture until water removal is complete gives a base product containing 0.8 mole acetamide and 0.7 mole acetic acid. Another 0.1 mole is carried overhead. Analysis of overhead water and vent line scrubbers shows a total of 0.47 mole of ammonia is lost overhead corresponding to a 35 percent loss of ammonia based on ammonium acetate.

EXAMPLE 3

This example shows that when execess acid over ammonia is fed to the nitrile reactor, the yield to undesirable by-product ketone is substantially increased. Gaseous ammonia and acetic acid were fed through a preheat section to a heated reactor containing a fixed bed of phosphoric acid on alumina and the product was cooled to ambient temperature and analyzed by standard methods. The reactor was maintained at 450°C. and the contact time of the reactants was 4 seconds. In Run 1 at these conditions a ratio of acid to ammonia of 1.11/1 was maintained in the feed. Acetone was formed at the rate of 0.027 mole per mole of acid fed. Run 2 was made at these same conditions except the acid to ammonia ratio was 0.9/1 in the feed. In this run acetone was formed at the rate of 0.0076 mole per mole of acid fed. This represents a 3.6 fold decrease in acetone formation by operating with a 10 percent excess of ammonia and avoiding excess acid.

EXAMPLE 4

This example illustrates that in the dehydration of ammonium acetate without a catalyst at 200°C. in the presence of excess acid a substantial amount of ammonia is lost overhead. A mixture containing 4.53 moles ammonium acetate and 0.35 mole of acetic acid, which is an 8 percent molar excess of acid, was fed continuously over a 4 hour period to a 6 foot packed column at a point 2 feet from the base. The base pot was operated with a volume of 275 ml and at 200°C. and the overhead at 100° to 105°C. The base product contained 21.5 percent free acetic acid at the end of the run with the remainder being primarily acetamide. A total of 0.74 mole of ammonia was taken overhead which represents a loss of 16 percent of the ammonium acetate to ammonia.

EXAMPLE 5

This example illustrates that when ammonium acetate is generated by the reaction of anhydrous acetic acid with ammonia and dehydrated to acetamide all in one step, a substantial loss of ammonia occurs even with 33 percent excess acid in the feed. The reactor consisted of a 5 foot packed column with the feed point 1.5 feet above the base pot. The base pot was a one liter flask and the liquid level was held at 400 ml. The base temperature was 185° to 186°C. and the overhead was 100° to 105°C. In a 5 hour run a total of 11.2 moles of acetic acid and 8.43 moles of ammonia was fed to the unit. This represents an excess of 33 percent acid. A total of 0.5 mole ammonia was taken overhead which represents a 6 percent loss of ammonium acetate to ammonia. The base contained 2.8 moles of acetic acid and 7.85 moles acetamide.

While the reaction illustrated is for acetic acid with ammonia to produce acetonitrile, the process according to our invention is useful with aliphatic acids containing from 2 to 6 carbon atoms to produce aliphatic nitriles having the corresponding number of carbon atoms. These include, in addition to acetic acid, propionic acid, n-butyric acid, isobutyric acid, pentanoic acid, and hexanoic acid.

Applicants have disclosed and described in detail a process for producing nitriles from the reaction of ammonia with an aliphatic carboxylic acid in which the loss of ammonia from the process steps is minimized. Thus, the yield of product from the ammonia utilized is increased, a desirable and useful end result.

The invention has been described in detail with particular reference to preferred embodiments thereof, but it will be understood that variations and modifications can be effected within the spirit and scope of the invention.

We claim:

1. Improved process for the production of an aliphatic nitrile which comprises reacting over a supported catalyst gaseous ammonia with an aliphatic carboxylic acid selected from acetic acid, propionic acid, n-butyric acid, isobutyric acid, pentanoic acid or hexanoic acid at a ratio of ammonia to acid of about 1/1 to 1.15/1.0 to form a product composed of about 40 to 50 percent aliphatic nitrile, about 0.5 to 3 percent ketone, about 6 to 10 percent ammonium carboxylate salt, and the remainder being water, cooling the product to 50°C. and distilling the product at a head temperature at or slightly above the boiling point of the nitrile-water azeotrope to separate the aliphatic nitrile from the other products, the improvement comprising adding a portion of the aliphatic carboxylic acid normally fed directly to the nitrile reactor to the effluent stream from the reactor but before distillation at a ratio in the range of from about 1 mole of said aliphatic carboxylic acid portion to 1 mole ammonium carboxylate to about 4 moles of said aliphatic carboxylic acid portion to 1 mole ammonium carboxylate whereby no additional acid is added to the process and whereby less than 1 percent ammonia based on the ammonium carboxylate fed into the distillation column with the effluent stream escapes from the distillation column and whereby the acid portion fed to the reactor effluent is recycled to the reactor from the distillation system.

2. Process according to claim 1 wherein the nitrile reactor is operated at 350° to 500°C.

3. Process according to claim 1 wherein the ratio of said carboxylic acid portion to said ammonium carboxylate is about 2/1.

4. Process according to Claim 2 wherein a base stream containing about 41 to 62 percent water, about 16 to 45 percent of said carboxylic acid, and about 14 to 22 percent ammonium carboxylate is taken from the distillation column, the water is removed with an azeotroping agent to yield an effluent stream comprising said aliphatic carboxylic acid and the corresponding aliphatic amide which is recycled to the nitrile reaction.

5. A process according to claim 1 wherein said aliphatic carboxylic acid is acetic acid, the product is acetonitrile, and the catalyst is phosphoric acid on alumina.

* * * * *